(12) United States Patent
Rangsten et al.

(10) Patent No.: US 7,149,282 B2
(45) Date of Patent: Dec. 12, 2006

(54) X-RAY TUBE ELECTRODES

(75) Inventors: Pelle Rangsten, Storvreta (SE); Carolina Ribbing, Uppsala (SE); Klas Hjort, Uppsala (SE); Jonas Tirén, Uppsala (SE)

(73) Assignee: Radi Medical Technologies AB, Uppsala (SE)

( * ) Notice: Subject to any disclaimer, the term of this patent is extended or adjusted under 35 U.S.C. 154(b) by 811 days.

(21) Appl. No.: 10/363,134

(22) PCT Filed: Sep. 7, 2001

(86) PCT No.: PCT/SE01/01913

§ 371 (c)(1),
(2), (4) Date: Mar. 6, 2003

(87) PCT Pub. No.: WO02/21564

PCT Pub. Date: Mar. 14, 2002

(65) Prior Publication Data

US 2004/0008818 A1    Jan. 15, 2004

Related U.S. Application Data

(60) Provisional application No. 60/230,708, filed on Sep. 7, 2000, provisional application No. 60/230,707, filed on Sep. 7, 2000.

(51) Int. Cl.
*H01J 35/04* (2006.01)
*H01J 35/06* (2006.01)
*H01J 35/08* (2006.01)

(52) U.S. Cl. .............. 378/136; 378/119; 378/143
(58) Field of Classification Search ................ 378/64, 378/65, 68, 119, 121, 122, 129, 134, 136, 378/138, 143
See application file for complete search history.

(56) References Cited

U.S. PATENT DOCUMENTS 3,803,958 A * 4/1974 Fernandez-Moran .......... 83/15

(Continued)

FOREIGN PATENT DOCUMENTS

EP    1 058 286 A1    12/2000

(Continued)

*Primary Examiner*—Edward J. Glick
*Assistant Examiner*—Anastasia S. Midkiff
(74) *Attorney, Agent, or Firm*—Foley & Lardner LLP (57) ABSTRACT

A miniaturized X-ray source is disclosed. It comprises an anode structure (43) and a cathode structure (41), each having an essentially pointed portion (44, 42), wherein at least the pointed portions being directed towards each other and enclosed in a vacuum cavity (49). The anode structure has an essentially dome shaped structure having a first essentially flat part (46) surrounded by a second essentially flat part (48), connected by a wall section (47), such that said first and second parts are located at different levels. The pointed portion is provided on said first flat portion and having an extension such that the apex of said pointed portion does not extend beyond the level of said second essentially flat part. A method of making an X-ray source is also disclosed.

15 Claims, 7 Drawing Sheets

U.S. PATENT DOCUMENTS

| | | | |
|---|---|---|---|
| 4,126,803 A | | 11/1978 | Bader et al. |
| 5,153,901 A | * | 10/1992 | Shoulders .................. 378/119 |
| 5,729,583 A | | 3/1998 | Tang et al. |
| 5,940,469 A | * | 8/1999 | Hell et al. .................. 378/143 |
| 6,134,300 A | * | 10/2000 | Trebes et al. ............... 378/136 |
| 6,241,651 B1 | | 6/2001 | Smith et al. |
| 6,275,566 B1 | * | 8/2001 | Smith et al. ................ 378/122 |
| 6,289,079 B1 | * | 9/2001 | Chornenky et al. ......... 378/143 |
| 6,333,968 B1 | * | 12/2001 | Whitlock et al. ........... 378/136 |
| 6,477,233 B1 | * | 11/2002 | Ribbing et al. ............. 378/136 |
| 2003/0012339 A1 | * | 1/2003 | Kerslick et al. ............ 378/122 |

FOREIGN PATENT DOCUMENTS

| | | | |
|---|---|---|---|
| EP | 1 139 383 B1 | | 6/2002 |
| JP | 2000014810 A | * | 1/2000 |
| WO | WO 97/07740 A1 | | 3/1997 |
| WO | 98/44529 A1 | | 8/1998 |

* cited by examiner

X-RAY TUBE ELECTRODES

The present invention relates to electrodes (anodes or cathodes) for a miniaturized X-ray tube, a method of manufacturing such an electrode (cathode or anode), and an X-ray tube incorporating such electrodes.

BACKGROUND OF THE INVENTION

There are many examples in the prior art of miniaturized X-ray sources for medical purposes, in particular for in vivo treatment of various lesions, such as tumors, stenoses etc. They all have the problem in common of achieving as high an output power as possible in order to enable delivering a high enough and controlled radiation dose at the point of treatment. Often times the materials of manufacturing sets certain limits in this respect, since the active parts, the anode and the cathode, must be enclosed in a vacuum cavity, and the enclosure materials often absorb a good deal of the generated radiation, thereby decreasing the efficiency of the device.

It is known in the prior art to manufacture miniaturized X-ray cathodes in the form of structures having small diamond tips as X-ray emitting elements. An example of such a manufacturing method is disclosed in applicant's own U.S. provisional application Ser. No. 60/137,478 (corresponding to EP-00850097.7), the entire contents of which is incorporated herein by reference This known method comprises providing structured silicon substrates in which e.g. pyramidal pits or depressions are etched. Then boron doped diamond is deposited on the substrate on the side having the depressions, so as to form diamond tips having a pyramidal shape, buried in the silicon substrate. Sacrificial etching (e.g. using $HF:HNO_3$ 3:7) of the silicon from the side opposite the side where diamond was deposited, to a desired depth exposed the diamond pyramids.

In order to control the thickness of the silicon that remains after the sacrificial etching, the etching time and etching solution composition must be carefully controlled. Certain irregularities, both in surface structure and thickness can occur, which could render the finished cathode structures difficult to assemble, in particular by bonding techniques, with other components to form a complete X-ray source.

SUMMARY OF THE INVENTION

An object of the present invention is therefore to provide a miniaturized X-ray source that will permit a very high portion of the generated radiation to actually exit from the enclosure without any substantial losses due to absorption in the materials of construction.

This object is achieved by a device according to the invention, wherein at least a portion of the enclosure that forms the vacuum cavity is made of a material that is transparent to X-ray radiation. In particular the material is selected to be diamond. More specifically the anode is made of diamond in the shape of a pointed structure, and is integrated in the enclosure, in such a way that radiation emitted by the anode, will be directed through the enclosure portion made of diamond. This is in particular achieved by arranging the apex of the pointed anode above the surface of surrounding structures, such that radiation emitted from the anode passes above said surrounding structures. The anode can be partly covered with a heavy metal such as W, Au, Ir, Pt etc.

Still another object of the present invention is to provide an improved method of manufacture so as to be able to improve the quality of the resulting cathode structures. In particular the thickness of the supporting silicon layer should be controlled to a greater extent, and the contact surface to which other components are to be attached should be improved in terms of roughness, i.e it should exhibit a high degree of planarity. By enabling a sufficiently flat and planar surface to be made, a number of bonding methods can be used for connecting parts to the surface, e.g. adhesive bonding, anodic bonding, eutectic bonding, plasma assisted bonding. Also, the method is suitable for batch fabrication.

This object is achieved with method of manufacturing according to the present invention.

BRIEF DESCRIPTION OF THE DRAWINGS

The invention will now be described in detail with reference to the attached drawings in which

FIG. 10a–d schematically illustrates the manufacture of the domes shaped electrode structure of FIG. 4a.

DETAILED DESCRIPTION OF THE INVENTION

First the novel and inventive device according to the invention will be described.

Figure 1:
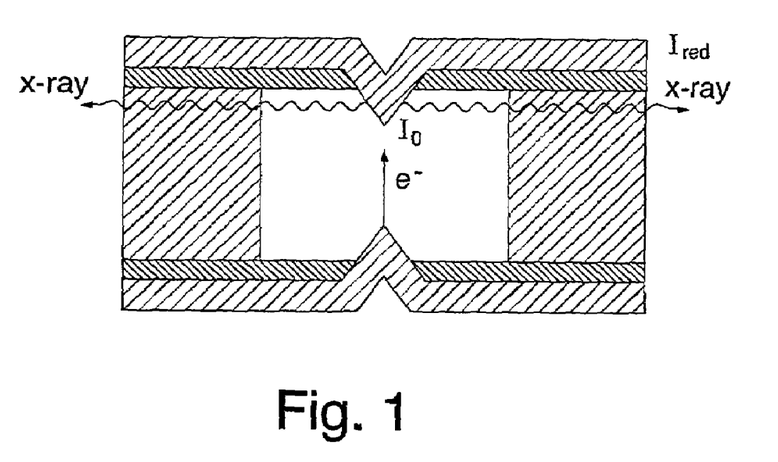
FIG. 1 shows a prior art X-ray source.
Figure 2:
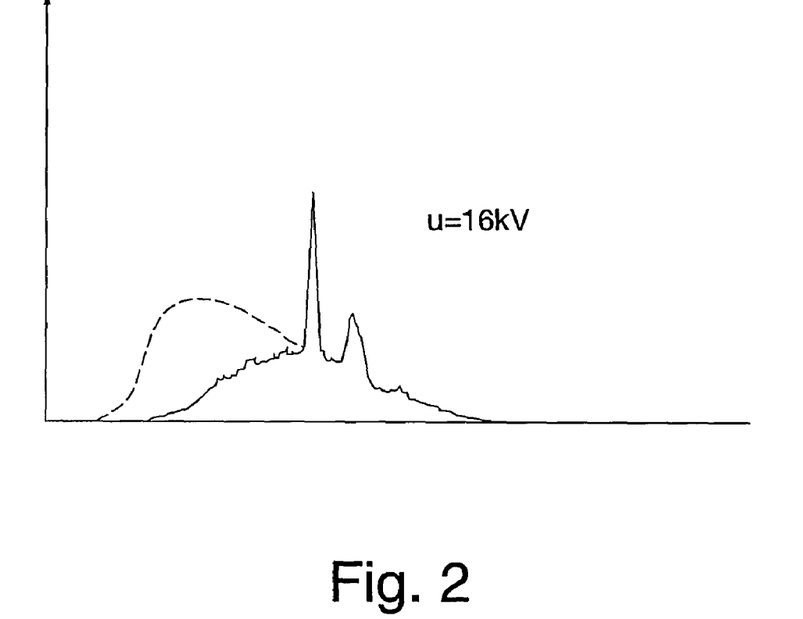
FIG. 2 shows a spectrum from a prior art source.
Figure 3:
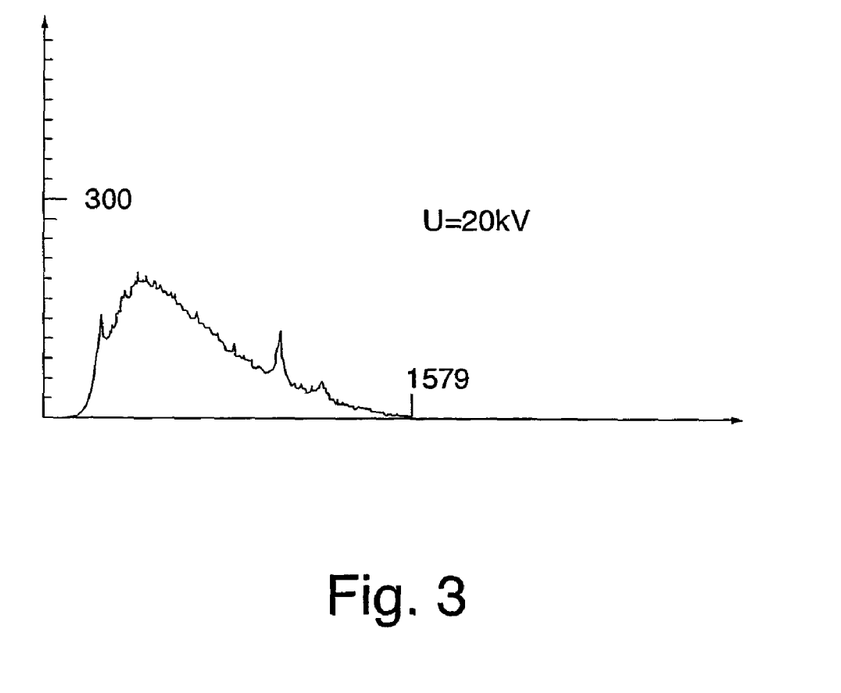
FIG. 3 shows a X-ray spectrum (Bremsstrahlung+characteristic peaks) from a source according to the invention.

The basic problem to be solved is that of avoiding absorption of radiation in the enclosing structures of a miniaturized X-ray source. FIG. 1 schematically shows a typical example of a miniaturized X-ray source exhibiting the absorption problem (In FIG. 6 a view of the cathode structure alone is shown). The generated radiation is partially absorbed in the insulating structure forming the enclosure. To appreciate the difference between prior art and the invention, consider FIGS. 2 and 3. FIG. 2 shows a spectrum from a prior art source, and FIG. 3 shows an X-ray spectrum (Bremsstrahlung+characteristic peaks) generated with a source according to the invention. As can be clearly seen, the Bremsstrahlung spectrum of the prior art device is significantly reduced in the lower kV range due to absorption in the chamber material, compared to the source according to the invention (unaffected profile indicated with broken line).

The new structure according to the invention will now be described with reference to FIG. 4a.

Thus, in a first embodiment a miniaturized X-ray source 40 according to the invention comprises a diamond cathode 41 having a pointed tip 42 (or an elongated sharp edge structure), a diamond anode 43 also having a pointed tip 44 (or a similar elongated sharp edge structure). The anode and cathode tips 42, 44 respectively are facing each other. The anode and cathode are spaced apart by means of insulating members 45, so as to form a cavity 49, that is evacuated. The cathode may be arranged as a free standing membrane, as indicated in the figure, and the insulator members 45 can be attached thereto by suitable means, e.g. various types of bonding techniques. However, it is also possible to manufacture the cathode 41 and the insulating spacer members 45 in one process to form a unitary structure.

The anode structure 43, likewise made of diamond, is different from the cathode 41, in that it is made to have an essentially dome like shape. Thus, the anode structure comprises a first central portion 46 in which the anode tip 44 is located. As already indicated the "tip" can be a pointed tip, e.g. a pyramid, or it can have an elongated shape, where the "tip" portion is an edge or a ridge like structure. The central portion 46 is surrounded by a wall section 47 connecting the central portion 46 with peripheral portion 48 such that the central portion 46 and the peripheral portion will be at different levels, and such that the anode "tip" 44 is located at a level between the level of the central portion and the peripheral portion. In other words, the entire anode structure could be looked upon as a "soup plate" having a circumferential edge portion essentially plane parallel with the bottom portion. In the bottom there is provided a protruding anode tip, the apex of which does not extend more than a fraction of the distance between bottom and edge. The wall section 47, while shown to have a certain inclination, can also be made essentially perpendicular to the bottom and periphery respectively. In fact, it would even be preferable to have an essentially perpendicularly oriented wall, since the radiation would than have to pass though a slightly thinner material section, with accompanying reduced losses.

The anode structure 43 can be coated on the peripheral circumferential portion 48, at least partially, but preferably around the entire periphey, with a metal 50, e.g. gold, to provide electrical contact, and also an intermediate surface for bonding purposes.

In particular, also the apex of the tip or pointed structure may be covered with a heavy metal such as W, Au, Ir, Pt etc. in order to increase the efficiency of the tip as an X-ray generator.

However, the major part of the flanks of the pointed tip 44 or ridge must not be covered, and neither must the side walls 47 of the enclosure in order that absorption be kept to a minimum. Electrical contact must however be provided, and is achieved by strips 51 of metal deposited as indicated in FIG. 4b. FIG. 4b shows an anode structure 43, seen from a direction corresponding to a view from within the cavity and separated from the cathode structure, and with a ridge embodiment of the anode tip 44. Here it is more clearly seen how the metal 50 is deposited on the apex region of the ridge structure. In the case of pyramidal tips a similar deposition is made, and also corresponding metal strips are deposited on the flanks of the tip (not shown). This strips 50 should preferably be made of a light metal, e.g. Al, in order to be more transparent to the X-rays emitted from the tip 44.

Figure 5:
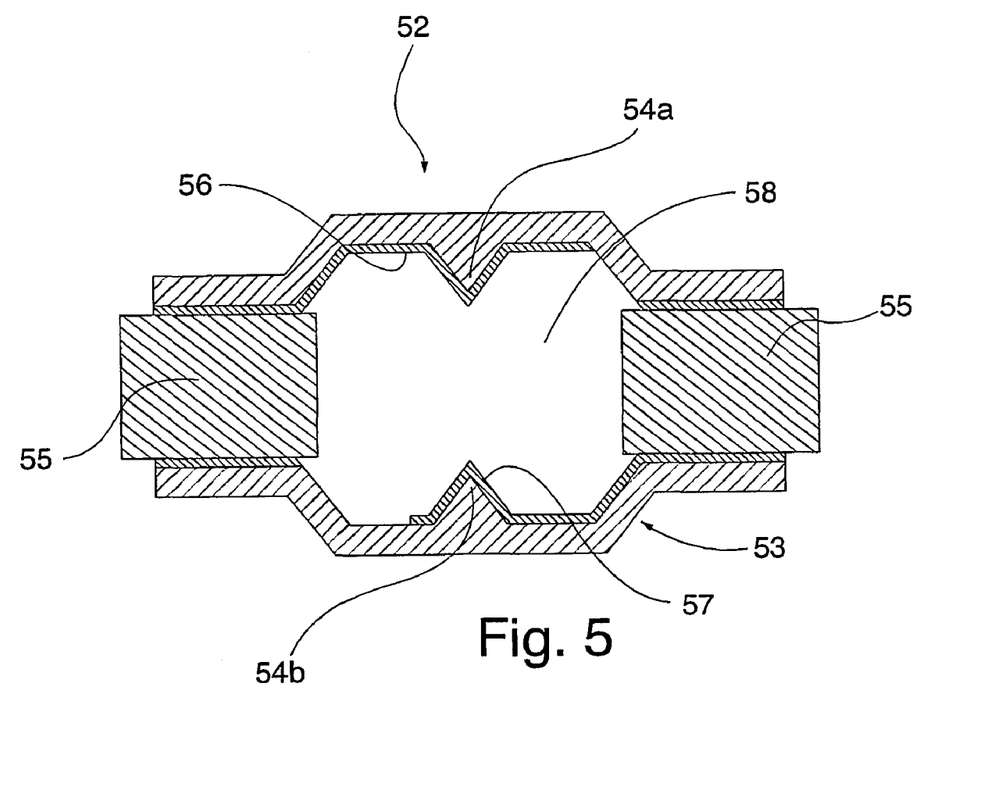
FIG. 5 shows an alternative embodiment of an X-ray device incorporating a cathode and an anode made according to the invention.

In alternative embodiment, shown in FIG. 5, the anode and cathode structures both have the above discussed dome like or "soup plate" like shape. In this embodiment the source must be operated according to the switching principle disclosed in our co-pending U.S. application Ser. No. 09/557,402 "A miniature X-ray tube with voltage selective electrodes".

This embodiment comprises a first dome shaped electrode structure 52 and a second dome shaped electrode structure 53, each having a pointed tip 54a and 54b, respectively, in the form of a pyramid or in the form of a ridge. Thus, they both correspond to the anode structure of FIG. 4a.

They are separated by an insulating member 55 forming a cavity 58, which is evacuated. Metal strips 56, 57 are deposited to provide electrical connection to an external voltage source (not shown). The choice of metals is based on the same considerations as for the embodiment of FIG. 4a.

As is illustrated with arrows in both embodiments, the emitted radiation will exit to the surrounding through the wall section 47 of the structure.

Figure 6:
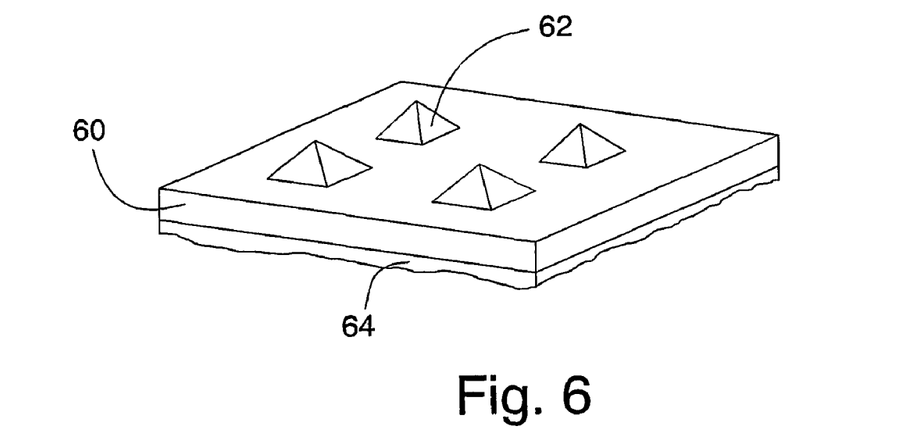
FIG. 6 shows a prior art cathode structure.

As already indicated above, FIG. 6 shows an X-ray cathode structure according to the above referenced U.S. provisional application serial No. 60/137,478. It comprises a silicon substrate 60 through which pyramid shaped diamond tips 62 protrude from a layer 64 of diamond deposited on the back side of said silicon substrate 1. It is made by providing a silicon wafer with an oxide layer; etching holes in the oxide layer; etching depressions in the silicon through the oxide; removing the oxide; depositing diamond over the depressions; etching away silicon to expose the diamond tips.

In said process, a number of factors will influence the end result. In particular the final etching that is performed in order to expose the diamond tips, is dependent on i.a. temperature, etchant composition and quality of the silicon that is to be etched away. I.a. the surface of the substrate 60 tends to have smoothness that is not optimal.

Figure 8A:
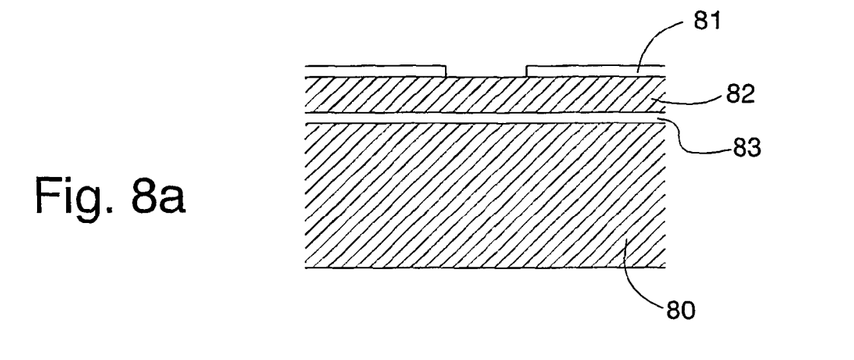
FIG. 8a–8e illustrates an inventive method of manufacture of a cathode structure according to FIG. 6.
Figure 8B:
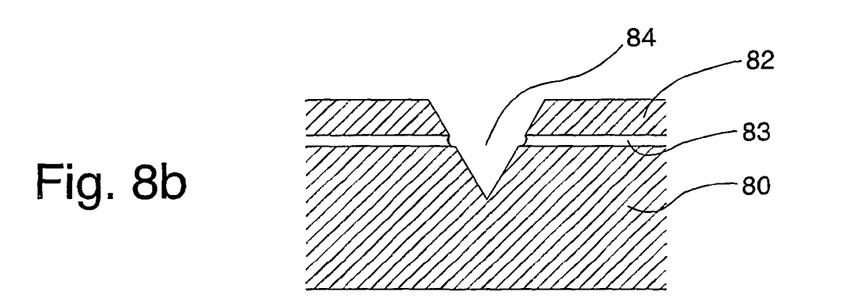
Figure 8C:
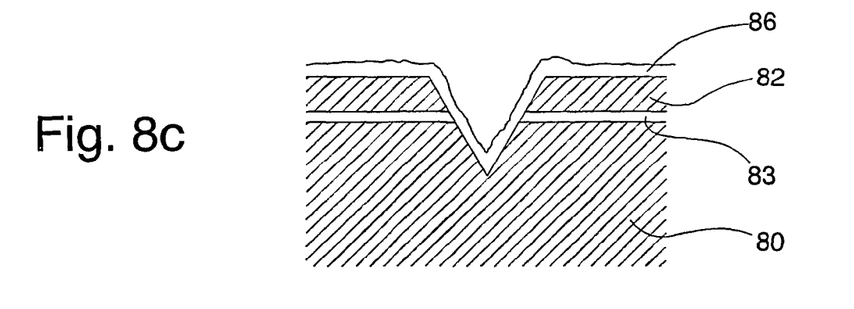
Figure 8D:
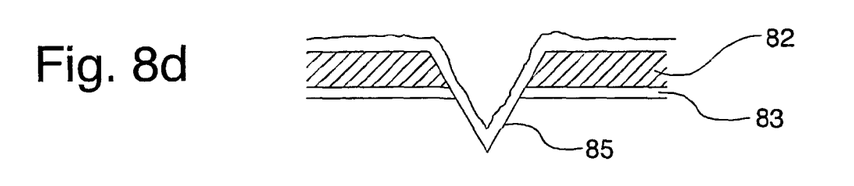
Figure 8E:
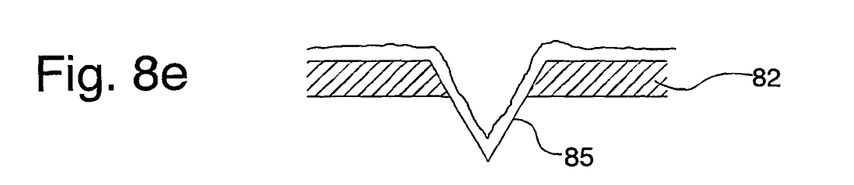

In order to obtain a controlled silicon thickness and a controlled surface structure (roughness and flatness), a cathode structure can be made in accordance with the invention by a process illustrated in FIGS. 8a–e, and the result of the inventive process is shown in FIG. 8e. In particular the surface will be flatter and smoother than what is obtainable with the prior art structure shown in FIG. 6.

Figure 7:
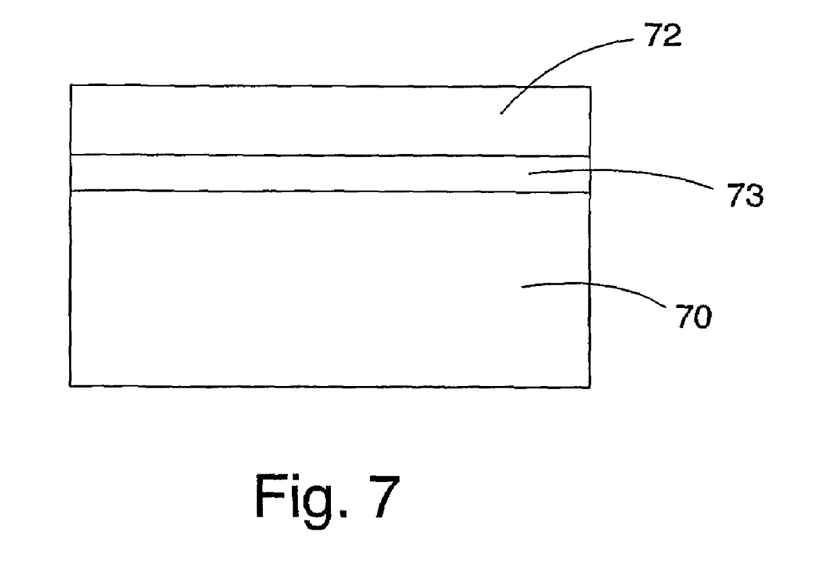
FIG. 7 shows an SOI structure as a starting material for a cathode structure according to FIG. 6.

Thus, in accordance with a further aspect of the invention, a so called SOI (Silicon On Insulator) substrate is provided. This is a conventional and commercially available type of starting material, used in the electronics industry for the manufacture of micro electronic devices. An SOI structure is shown schematically in FIG. 7. It comprises silicon substrate wafer (bottom layer) 70 and a silicon device layer (top layer) 72 sandwiched with an insulating silicon dioxide layer 73. The device layer 72 is typically 10–100 μm thick, and the silicon dioxide layer is typically 0,5 μm thick.

The process for the manufacturing of a miniaturized X-ray cathode structure according to the invention will now be described with reference to FIGS. 8a–e.

In this sequence of steps the method begins with processing of the top layer (device layer). Thus, by using lithographic methods, known per se, a mask layer 81 is deposited on the device (top) layer 82 of the SOI wafer (FIG. 8a). Next, wet or dry etching of the silicon is carried out through the device layer 82, insulator layer 83 and further into the substrate wafer 80 (FIG. 8b) to create pits 84 or depressions thereby forming a template for the diamond tips 85 to be made. After the template has been made, a diamond layer 86 (or other cathode/anode material e.g. diamond like carbon (DLC)) is deposited over the pattern of pits 84 (FIG. 8c).

In view of the presence of the insulating silicon dioxide layer 83, it is possible to use this layer as a stop layer, such that if the substrate wafer 80 is exposed to an appropriate etch solution, only the substrate wafer 80 will be etched away. This will leave a resulting structure (FIG. 8d) where the tip 85 protrudes through a very planar and flat surface.

In alternative process, the SOI is reversed, i.e. the mask is applied to the silicon wafer (bottom layer) instead, and the process steps are repeated.

This structure can be used as is, namely by utilizing the silicon dioxide layer 83 as the contact surface for various bonding procedures in assembling the structure together with other components. However, it is also possible to remove the silicon dioxide layer 83, and expose the bottom side of the top layer for bonding purposes.

The structure obtained by this process (i.e. the one shown in FIG. 8*d* or 8*e*) can be used for both anodes and cathodes in a miniaturized X-ray device.

Figure 9:
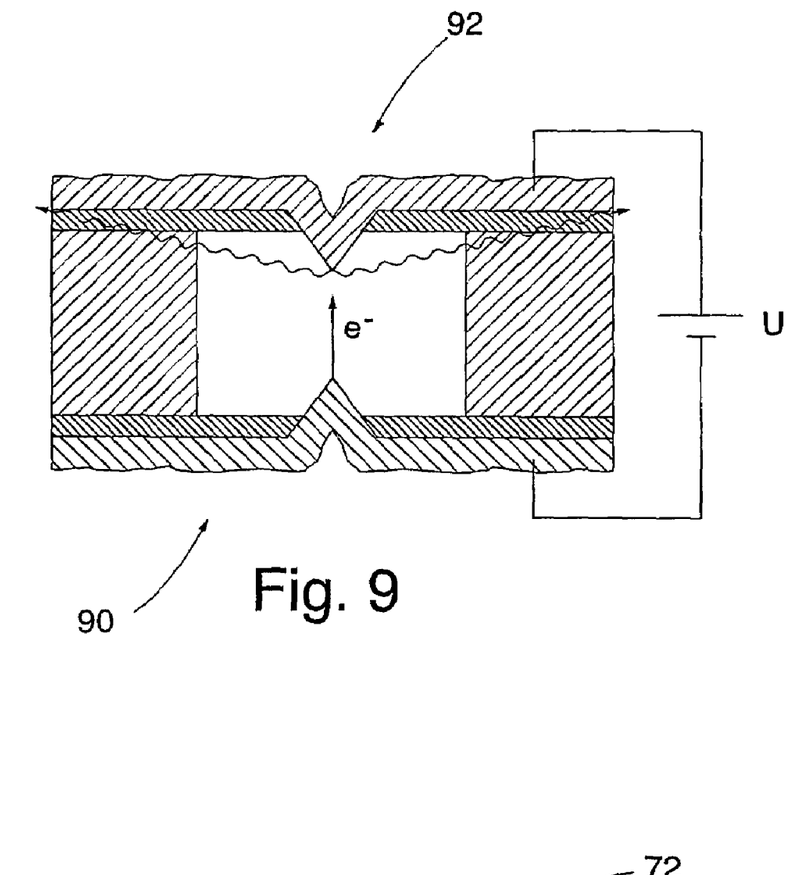
FIG. 9 illustrates an X-ray device made by combining electrodes made according to the method of FIGS. 8a–8e.

An example of a complete X-ray device wherein cathodes and anodes are made in accordance with the method disclosed herein is shown schematically in FIG. 9. It comprises a cathode 90 and an anode 92, having essentially the structure shown in FIG. 8*e* and arranged opposite each other such that the tips thereof point towards each other. A vacuum cavity is provided by providing spacer member to form walls (preferably of an insulating material) surrounding the electrode tips. The cathode should be provided with a heavy material such as W or Au, in order to achieve a higher X-ray output power.

A dome shaped anode/cathode structure can be made as described below with reference to FIGS. 10–10*d*.

Figure 10A:
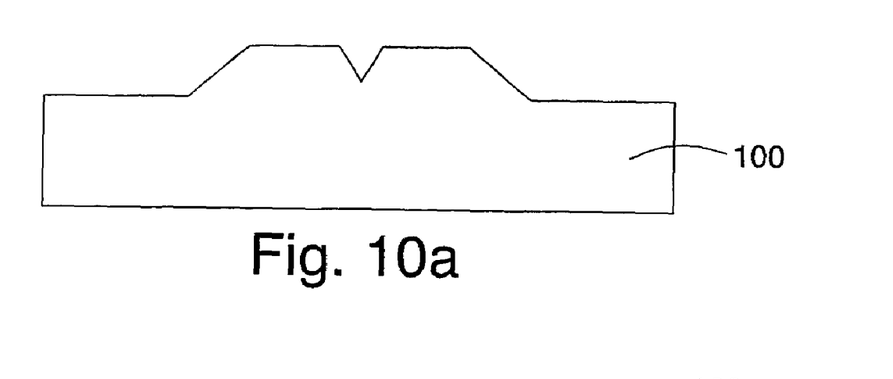
Figure 10B:
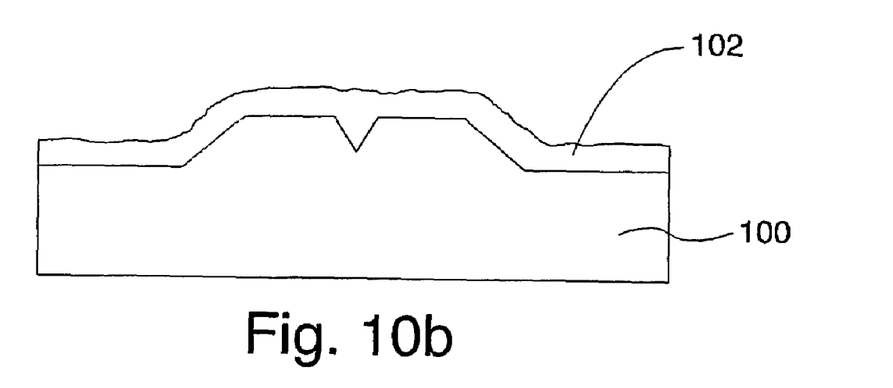
Figure 10C:
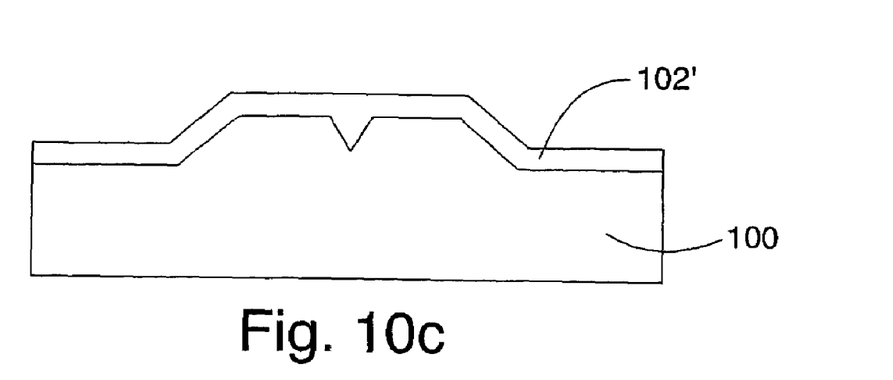
Figure 10D:
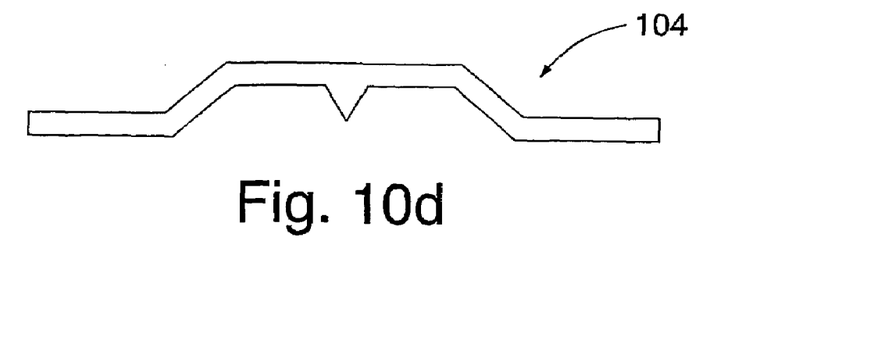

A silicon substrate is suitable masked and anisptropically etched (e.g. with KOH) to provide a template 100 as shown in FIG. 10*a*. The skilled man will know how to suitably select proper etchants and suitable templates to obtain the desired structures of the templates, and this will not be discussed in detail herein. Then, diamond 102 is deposited to cover the shaped surface, see FIG. 10*b*. The diamond layer 102' is suitably thinned and polished to a higher smoothness. Finally the silicon is removed by sacrificial etching to leave a free standing diamond membrane 104.

Two membranes obtained by this method can be attached by bonding to an insulating structure to form a device such as the one shown in FIG. 5.

Figure 4A:
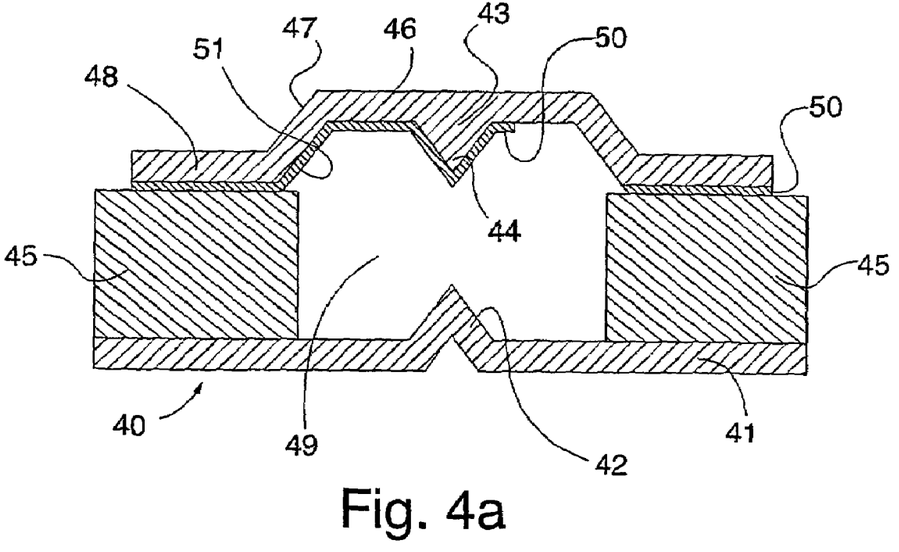
FIG. 4a shows an embodiment of the X-ray source according to the present invention.
Figure 4B:
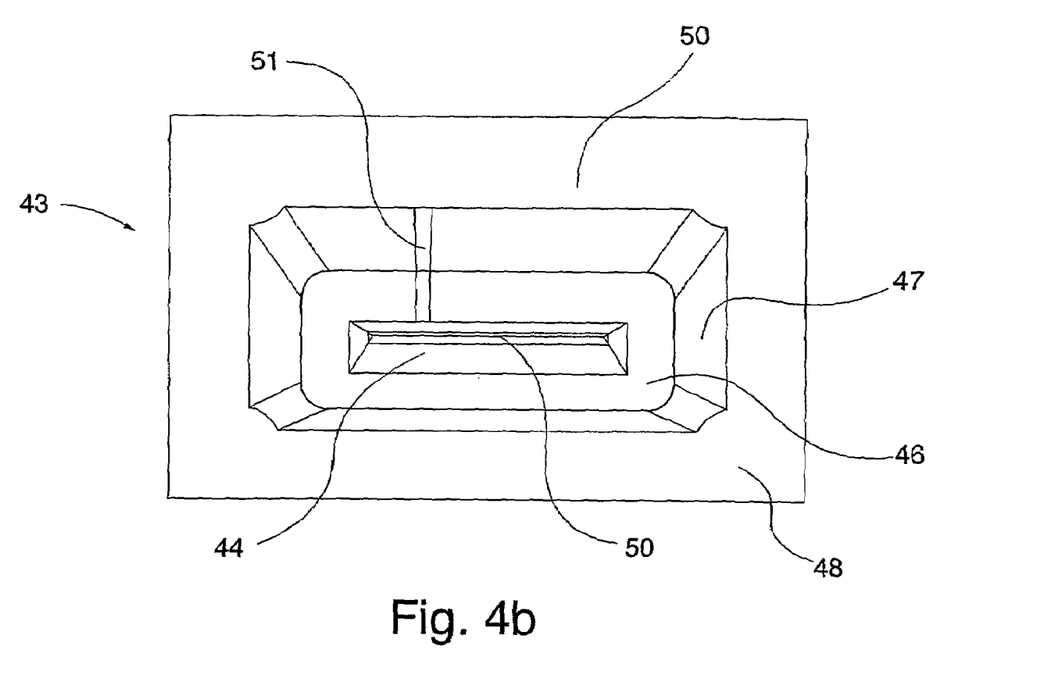
FIG. 4b is a view from beneath of only a dome shaped diamond membrane.

Alternatively, one such structure can be combined with a prior art type cathode structure, and an intermediate insulating structure, to form a device like the one shown in FIG. 4*a*.

The dome shaped anode/cathode structures have herein been illustrated to have sloping side walls (see FIG. 4*a* and FIG. 5). The reason for this is mainly because it is easier to manufacture such a structure. From a radiation efficiency point of view it would be better to have a cylindrical dome, since that would enhance transmission of radiation. Thus, a cylindrical dome shape is also within the inventive concept.

The invention claimed is:

1. A miniaturized X-ray source, comprising
   an anode structure having an essentially pointed first portion, and a cathode structure having an essentially pointed second portion, said pointed portions being directed towards each other and being enclosed in a vacuum cavity; wherein furthermore
   at least said anode structure has an essentially dome shaped structure having a first essentially flat part surrounded by a second essentially flat part, connected by a wall section, such that said first and second parts are located at different levels;
   said pointed first portion is provided on said first flat part and having an extension such that the apex of said pointed portion does not extend beyond the level of said second essentially flat part.

2. The X-ray source of claim 1, wherein the cathode structure has the same configuration as the anode structure.

3. The X-ray source of claim 1, wherein the anode and cathode material is an X-ray transparent material.

4. The X-ray source of claim 1, wherein the anode is partly covered with a heavy metal.

5. The X-ray source of claim 1, wherein the dome shaped structure has side walls that are essentially perpendicular to said first and/or second flat parts.

6. The X-ray source of claim 1, wherein the dome shaped structure has sloping side walls.

7. The X-ray source of claim 4, wherein the metal is deposited as narrow strips on the inside of at least one of the anode and the cathode so as to form conductors, connectable to an external power source.

8. The X-ray source of claim 7, wherein the metal is a light metal.

9. The X-ray source of claim 1, wherein there is provided an intermediate metal layer between at least one of the anode and the cathode and an insulating material.

10. A method of making an X-ray source according to claim 1, comprising
    masking and etching a silicon substrate to provide a template having a surface of a shape corresponding to the desired dome shape;
    depositing diamond to cover the shaped surface;
    thinning and polishing the diamond layer to a higher smoothness;
    removing the silicon by sacrificial etching to leave a free standing diamond membrane;
    attaching said diamond membrane by bonding to an insulating structure having a through hole therein, such that said membrane covers said through hole, thereby forming an anode;
    attaching a cathode structure to cover said through hole on the opposite side of said insulating structure, thereby forming a cavity; and
    evacuating the cavity.

11. The method of claim 10, wherein the cathode is made in the same way as the anode, whereby the anode is operable as a cathode and the cathode is operable as an anode by switching the polarity of an external voltage source at a predetermined frequency.

12. The method of claim 10, wherein the material in the top and bottom layers is silicon.

13. The method of claim 10, wherein the material in the intermediate layer is silicon dioxide.

14. The method of claim 10, wherein tips of said diamond membrane are shaped as pyramids.

15. The method of claim 10, wherein tips of said diamond membrane are shaped as elongated members having a sharp top edge.

* * * * *